United States Patent [19]
Remar et al.

[11] Patent Number: 5,548,003
[45] Date of Patent: Aug. 20, 1996

[54] AZOLE-ALDEHYDE ADDITION PRODUCT EMBOSSING INHIBITORS AND THE USE THEREOF

[75] Inventors: Joseph F. Remar, Lancaster; Carl E. Sideman, Lititz, both of Pa.

[73] Assignee: Armstrong World Industries, Inc., Lancaster, Pa.

[21] Appl. No.: 515,110

[22] Filed: Aug. 14, 1995

[51] Int. Cl.[6] .............. C08K 5/3475; C08K 5/3447; C07D 235/02; C07D 249/20
[52] U.S. Cl. .............. 523/160; 523/161; 524/91; 524/93; 548/260; 548/310.1
[58] Field of Search ............... 523/160, 161; 524/91, 93; 548/260, 310.1

[56] References Cited

U.S. PATENT DOCUMENTS

| | | | |
|---|---|---|---|
| 3,293,094 | 12/1966 | Naim et al. | 156/79 |
| 4,083,907 | 4/1978 | Hamilton | 264/52 |
| 4,191,581 | 3/1980 | Hamilton | 106/20 |
| 4,369,065 | 1/1983 | Brixius | 106/27 |
| 4,407,882 | 10/1983 | Hauser et al. | 428/159 |
| 4,408,049 | 10/1983 | Gall | 544/366 |
| 4,421,561 | 12/1983 | Brixius | 106/27 |
| 4,421,753 | 12/1983 | Tomcufcik et al. | 544/366 |
| 4,522,785 | 6/1985 | D'Errico | 252/390 |
| 4,788,292 | 11/1988 | Clark et al. | 548/260 |
| 5,169,435 | 12/1992 | Sherman et al. | 106/20 |
| 5,254,159 | 10/1993 | Gundlach et al. | 106/22 |
| 5,328,625 | 7/1994 | Farng et al. | 548/260 |
| 5,336,693 | 8/1994 | Frisch | 521/72 |
| 5,441,563 | 8/1995 | Sideman et al. | 106/224 |

FOREIGN PATENT DOCUMENTS

| | | |
|---|---|---|
| 1466558 | 3/1977 | United Kingdom . |

OTHER PUBLICATIONS

Mozolis, V. V. and Jokubaityte, S. P., "The Benzotriazole and Thiourea in Mannich Reaction", *Works of the Academy of Scs. of the Lithuanian SSR*, Ser. B, vol. 1(60), (1970).

Katritzky, A. R. et al, "Reactions of Benzotriazole with Formaldehyde and Aliphatic Primary Amines", *J. Chem. Soc.*, (1990), pp. 541–547.

Katritzky, A. R. and Hughes, C. V., "The Chemistry of N–Substituted Benzotriazoles", *Chemica Scripta*, vol. 29, (1989), pp. 27–31.

Katritzky, A. R. et al, "The Chemistry of N–Substituted Benzotriazoles, Part 2, Reactions of Benzotriazole with Aldehydes etc.", *J. Chem. Soc.*, (1987), pp. 791–797.

Burckhalter, J. H. et al, *J. Am. Chem. Soc.*, (1952), vol. 74, pp. 3868–3870.

*Primary Examiner*—Veronica P. Hoke

[57] ABSTRACT

Solid aromatic or cycloaliphatic azole-aldehyde addition products can be used as chemical embossing inhibitors. Most of the addition products can be readily micronized and dispersed into water-based printing inks for use in producing textured foamed plastic surfaces. These compounds comprise a general class of adducts of azole derivatives (benzotriazole and benzimidazole) reacted with aldehydes.

6 Claims, No Drawings

AZOLE-ALDEHYDE ADDITION PRODUCT EMBOSSING INHIBITORS AND THE USE THEREOF

FIELD OF THE INVENTION

The invention relates to blowing agent inhibitors and their use. In particular, the invention is directed to azole-aldehyde addition products which are effective blowing agent inhibitors. Most of the inhibitors are capable of being ground and dispersed in situ in an ink composition.

BACKGROUND OF THE INVENTION

It is well known to those skilled in the art that foamed plastic surfaces may be textured by the process commonly referred to as "chemical embossing", wherein the surface of a foamable polymer composition is printed with an ink composition containing an agent which inhibits foaming in the printed areas when the foamable polymer composition is subsequently subjected to a heat treatment. The areas which have not been printed over thus expand normally on heating while expansion in the printed areas containing the inhibitor is retarded, resulting in a textured surface with depressions in those areas printed with the inhibited ink.

A wide range of compounds have been claimed to act as inhibitors for chemical embossing of floor and wall covering surfaces, including azole derivatives of benzotriazole, tolyltriazole and benzimidazole derivatives such as disclosed in copending Sideman et al. U.S. patent application Ser. No. 271,633, filed Jul. 7, 1994, now U.S. Pat. No. 5,441,563, issued Aug. 15, 1995, which application is incorporated by reference.

SUMMARY OF THE INVENTION

In the present invention, azole-aldehyde addition products have been found to be crystalline solids. Most of these derivatives can be readily micronized and dispersed into aqueous inks of widely varying composition with no adverse impact on the stability of the ink or its printing and drying characteristics. Further, with the exception of benzotriazol-1-yl(hydroxy)acetic acid (BTA-HAA), these derivatives can be dispersed into typical ink compositions and ground in situ without adverse effects on the ink composition. BTA-HAA destabilized an aqueous ink composition, but was effective in a solvent-based ink composition.

The term "azole" as used herein includes benzotriazole, tolyltriazole, naphthotriazole, cycloaliphatic triazole, benzimidazole, tolylimidazole, naphthimidazole and cycloaliphatic imidazole derivatives.

Accordingly, an object of the present invention is to provide an inhibitor for water-based and solvent-based inks which do not interfere with the ink stability or drying characteristics of the ink composition. Therefore, the liquid ink has excellent shelf-life and dries without becoming tacky.

It is also an object of the present invention to provide a printing ink composition for the production of textured foamed surfaces, which composition comprises a binder resin, solvent, and a blowing agent inhibitor having the general formula (I) below:

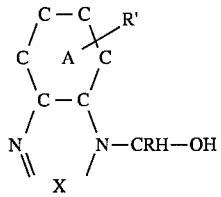

wherein the A ring is benzenoid, naphthenoid or saturated cycloaliphatic, the A ring being unsubstituted or substituted with R' which is an alkyl group of 1 to 4 carbon atoms; R being a hydrogen atom; an aryl, an alkyl, a haloalkyl, a haloaryl or a 4-pyridyl radical; or a carboxy group; X being a nitrogen atom or the

group, wherein R' is a hydrogen atom or an alkyl group of 1 to 4 carbon atoms. In some preferred embodiments R is hydrogen or a $C_1$ to $C_8$ alkyl group, more preferably hydrogen or a $C_1$ to $C_4$ alkyl group, and most preferably hydrogen. When R is an aryl group, it is preferably pyridyl. Generally when R is hydrogen, the compound is a high melting solid, and when R is an alkyl group, the compound is a low melting solid.

It is an additional object of the present invention to provide a printing ink composition for the production of textured foamed surfaces, which composition comprises a binder resin, solvent, and a blowing agent inhibitor having the formula (II) below:

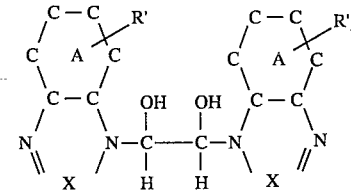

wherein the A ring is benzenoid, napthenoid or saturated cycloaliphatic, the A ring being unsubstituted or substituted with R' which is an alkyl group of 1 to 4 carbon atoms; X is a nitrogen atom or the

group, wherein R' is a hydrogen atom or an alkyl group of 1 to 4 carbon atoms.

Another object is to provide two new compounds, 1hydroxymethyl tolyl triazole and 1-hydroxymethyl methyl cyclohexyl triazole.

A further object of the invention is to provide a method of embossing a heat-foamable resinous material by applying the printing ink composition of the present invention to selected areas of the surface of a heat-foamable resinous material, which material contains a blowing agent, and subsequently heating the material to or above the decomposition temperature of the activated blowing agent.

DETAILED DESCRIPTION OF THE INVENTION

The preferred structures of the azoles of this invention are those of Formula I in which the A ring is a benzenoid, R is hydrogen, R' is hydrogen or methyl and X is a nitrogen atom.

For acceptable processing, it is advantageous to use 1 to 15 percent by weight of the azole dispersed in the aqueous printing ink composition, and preferably 5 to 10 percent by weight for floor covering applications. Higher concentrations can be used (>15%) depending on the application weight of the wet applied ink. Shallower engraved cylinders may require more inhibitor per unit area to get the desired embossed effect.

Those skilled in the art will recognize that a very wide range of printing ink compositions exist with varying combinations of resin binders, pigments, inhibitors and rheology-control additives. They will also recognize that varying amounts of water and/or solvent will be required to adjust the viscosity of the ink composition to a range suitable for typical rotogravure printing. Other methods of printing the ink composition onto the foamable plastic surface, such as screen printing, relief printing, or planographic printing, may also be used with these ink compositions.

Although this invention is primarily concerned with polyvinylchloride-based plastisol compositions thermally blown with azodicarbonamide or other blowing agents as the printing substrate, there likewise exists a wide range of resins which can be thermally foamed with azodicarbonamide and thus are potential substrates for aqueous inhibitor printing ink compositions of the type claimed. Such other compositions include polyvinyl acetate, copolymers of vinyl chloride and vinyl acetate, polyacrylate, polymethacrylate, polyethylene, polystyrene, butadiene/styrene copolymers, butadiene/acrylonitrile copolymers, and natural or synthetic rubbers.

The specific combinations of PVC, other resins, filler, stabilizers, plasticizers, chemical blowing agents and activators that make up a typical foamable plastisol substrate vary widely within certain limits and those skilled in the art can reasonably anticipate systems which would be encompassed by the scope of this invention.

The invention is illustrated by the following examples related to synthesis of the azole derivatives, preparation of the aqueous dispersions and printing ink formulations, and demonstration of the chemical embossing behavior of the claimed compounds. Unless otherwise stated, all amounts and percentages given in the Examples are on a weight basis.

EXAMPLE 1

Preparation of 1-(1-Hydroxyethyl) Benzotriazole (HEBTA)

Benzotriazole (59.5 parts, 0.5 moles) was dissolved in boiling diethyl ether and acetaldehyde (88 parts, 2.0 moles) in diethyl ether was added. The reaction mixture was kept at 25° C. for 12 hours. The system was filtered, the solid washed with pentane and dried in vacuum to yield 63.1 parts (77.4% yield) of a solid melting at 82°–85° C. (literature[1], m.p. 74°–5° C.). An additional 8.6 parts (10.5% yield) was obtained by dilution of the filtrate with hexane and cooling in a refrigerator at −5° C., followed by filtration and drying in vacuum. The resulting material was identified by NMR as 1-(1-hydroxyethyl) benzotriazole.

[1]A. R. Katritzky et al., J. Chem. Soc., Perkin Trans, 1, 1987, 791–7. Note the melting points published are consistently low compared to the measured melting points and literature[2].
[2], R. Burckhalter et al., J. Am. Chem. Soc., 1952, 74, 3868.

EXAMPLE 2

1-Hydroxymethyl Benzimidazole (HMBI)

A sample of 1-Hydroxymethyl benzimidazole was supplied by Interchem Corporation, Paramus, N.J.

EXAMPLE 3

Preparation of 1,2-Dibenzotriazol-1-yl Ethane-1, 2-Diol (BTG-D)

Sulfuric acid (20 drops) was added to 400 parts of acetic acid slowly. Benzotriazole (59.6 parts, 0.5 moles) was added and the mixture was stirred and heated to 75° C. A 40% aqueous solution of glyoxal (36.3 parts) was added and a white solid started to precipitate. After all the glyoxal had been added, the reaction was allowed to sit at 25° C. for 24 hours. The solid was filtered, washed with acetic acid, washed twice with water, and dried at 60° C. in a vacuum oven. The yield was 67.3 parts (91% yield) of a white solid melting at 192°–5° C. (literature[1], m.p. 167°–9° C.). The resulting material was identified by NMR as 1,2-dibenzotriazol-1-yl ethane-1,2-diol.

[1]A. R. Katritzky et al., J. Chem. Soc., Perkin Trans, 1, 1987, 791–7. Note the melting points published are consistently low compared to the measured melting points and literature[2].
[2], R. Burckhalter et al., J. Am. Chem. Soc., 1952, 74, 3868.

EXAMPLE 4

Preparation of 1-Hydroxymethyl Benzotriazole (HMBTA)

Benzotriazole (120 parts, 1.01 moles) was added to a flask and a mixture of 100 parts of acetic acid and 200 parts of water was added to the flask with stirring. After the benzotriazole had dissolved, 86.6 parts (1.07 moles) of a 37% aqueous solution of formaldehyde was added. After about 5 minutes mixing, a white solid formed. After stirring 2 more hours, the reaction mixture was cooled in an ice bath. The solid was filtered, washed with cold deionized water and dried in a vacuum oven. The crude product was recrystallized from ethyl acetate (2700 parts) to yield 102 parts (68% yield) of a solid melting at 148°–52° C. (literature[1], m.p. 135°–7° C.; literature[2], m.p. 148°–51° C.).

The resulting material was identified by NMR as 1-hydroxymethyl benzotriazole.

[1]A. R. Katritzky et al., J. Chem. Soc., Perkin Trans, 1, 1987, 791–7. Note the melting points published are consistently low compared to the measured melting points and literature[2].
[2], R. Burckhalter et al., J. Am. Chem. Soc., 1952, 74, 3868.

EXAMPLE 5

Preparation of Benzotriazol-1-yl-(4-pyridyl)methanol (BTA-PCA)

Benzotriazole (23.8 parts, 0.2 moles) and 4-pyridine carboxaldehyde (26.8 parts, 0.25 moles) were dissolved in the minimum amount of THF. The product crystallized as prisms which were filtered off, washed with diethyl ether and dried in vacuum at 25° C. to give 39.0 parts (86% yield) of a material melting at 110°–2° C. (literature[1], m.p. 103°–4° C.). The resulting material was identified by NMR as benzotriazol-1-yl-(4-pyridyl)methanol.

[1]A. R. Katritzky et al., J. Chem. Soc., Perkin Trans, 1, 1987, 791–7. Note the melting points published are consistently low compared to the measured melting points and literature[2].
[2], R. Burckhalter et al., J. Am. Chem. Soc., 1952, 74, 3868.

EXAMPLE 6

Preparation of 1-Hydroxymethyl Tolyl Triazole (HMTTA)

5-Methyl-1,H-benzotriazole (20 parts) was dissolved in 20 ml. of acetic acid. Water (40 parts) was added and then 16.2 parts of a 37% aqueous formaldehyde solution was added dropwise with stirring. The reaction was allowed to run two hours, cooled in an ice bath, filtered, and washed with cold deionized water. The resultant white solid was dried in a vacuum oven with $P_2O_5$ overnight to yield 23.2 parts of a solid melting at 125°–8° C. Structural confirmation was made by $^1H$ and $^{13}C$ NMR spectral analysis and the material was identified as 1-hydroxymethyl tolyl triazole.

EXAMPLE 7

Preparation of 1-Hydroxymethyl Methyl Cyclohexyl Triazole (HMHTTA)

Hydrogenated 5-Methyl-1,H-benzotriazole (20.6 parts from PMC Specialties) was added to a flask and 20 parts of acetic acid and 40 parts of water were added to the flask with stirring. After the triazole had dissolved, a 37% aqueous solution of formaldehyde (12.9 parts) was added dropwise with stirring. The reaction was allowed to proceed two more hours and was then made basic with a 10% aqueous sodium hydroxide solution. The system was filtered and concentrated. The concentrate was taken and triturated with 100 ml. of petroleum ether and put in a –5° C. refrigerator overnight. The solid was filtered, washed with cold petroleum ether, and dried in a vacuum oven to yield 21.3 parts of a solid with a m.p. 48°–50° C. Structural confirmation was made by $^1H$ and $^{13}C$ NMR spectral analysis and the material was identified as to be 1-hydroxymethyl methyl cyclohexyl triazole.

EXAMPLE 8

Preparation of Benzotriazol-1-yl(Hydroxy)Acetic Acid (BTA-HAA)

Benzotriazole (59.5 parts, 0.5 moles) was dissolved in 150 parts of acetic acid at 70° C. Sulfuric acid (5 drops) was added, followed by 74 parts (0.5 moles) of 50% aqueous glyoxylic acid. The mixture was heated to 80° C. for 30 minutes and then kept at 25° C. for 12 hours. The system was cooled at –5° C. for 48 hours, filtered, washed with toluene three times and put in a vacuum oven to dry. The yield was 49.1 parts (49.2% yield) of white needles, melting at 150°–3° C. (literature[1], m.p. 136°–7° C.). The resulting material was identified by NMR as benzotriazol-1-yl(hydroxy)acetic acid.

[1] A. R. Katritzky et al., J. Chem. Soc., Perkin Trans, 1, 1987, 791–7. Note the melting points published are consistently low compared to the measured melting points and literature[2].
[2] R. Burckhalter et al., J. Am. Chem. Soc., 1952, 74, 3868.

The following procedure was used to disperse the compounds of Examples 1 to 7 into various ink vehicles. Instead of pregrinding and then dispersing the inhibitors, they were ground and dispersed in situ in a water-based ink extender. A sixteen ounce HDPE bottle was filled halfway with a mixture of 12 mm diameter spherical and 6 mm diameter ×6 mm high cylindrical ceramic balls. To the bottle was added 21.6 grams of the coarse inhibitor powder and then 158.4 grams of extender CIE 94 manufactured by Penn Color, Inc. This gave a concentration of 12% by weight of the compounds and room to adjust the concentration and viscosity with water and more extender. The charged mill was rolled overnight (about 18 hours) and checked for the quality of the dispersion. The ceramic balls were separated from the dispersion and the dispersion was adjusted to 10% by weight of the compound with water and additional extender to a viscosity of 15 seconds with a #3 Zahn Cup.

Example 8 was dispersed in the same manner as Examples 1 to 7. However, because of incapability with extender CIE 94, a solvent-based extender (Extender 5Q3204, manufactured by Del Val Ink and Color, Inc.) was used.

Table I sets forth a number of properties of Examples 1 to 8 which were made and tested. Inks were made with these compounds using the direct milling procedure and then evaluated for printing, drying and embossing characteristics.

The inhibited inks (at 10% by weight inhibitor concentration) were printed on 7 mils of an expandable plastisol coated onto a glass mat which was saturated with a non-expandable plastisol. This was done on a flat-bed gravure proof press using a 100 line screen step-wedge gravure plate. The steps ranged from a deep shadow tone to a shallow highlight tone. The inks printed and dried without any tack.

The printed samples were coated with 10 mils of a clear plastisol wearlayer and heated for 1.9±0.1 minutes at an air temperature of 185°±2° C. in a Werner Mathis oven to fuse and expand the foamable plastisol to about 14 mils (a 2:1 blow ratio). The thickness of the printed coated areas (i.e., restricted areas) was measured in mils and compared to the thickness of the expanded unprinted surrounding areas. This difference was recorded as depth of chemical embossing and was used along with the degree of expansion in the inhibited area to assess the inhibitor activity (IA).

The inhibitor activity of N-(benzotriazol-1-yl methyl) 4'-carboxybenzene sulfonamide (BTA-4CBSA), Example 34 of Sideman et al. U.S. patent application Ser. No. 271,633, now U.S. Pat. No. 5,441,563, was used as the benchmark and on a scale of 1 to 5 was given a rating of 1 (five on the scale being less than one mil of overall chemical embossing). This is a subjective ranking where the other compounds were evaluated for inhibitor activity by comparing them to BTA-4CBSA, both numerically and visually.

TABLE I

| EXAMPLE | | | | | FORMULA (I) | | |
|---|---|---|---|---|---|---|---|
| No. | Abv. | IA[a] | MW | MP °C. | X | R | A–R' |
| 1 | HEBTA | 2 | 163 | 82-5 | N | $CH_3$ | Phenyl |
| 2 | HMBI | 3 | 148 | 140-3 | CH | H | Phenyl |
| 3 | BTG-D | 2 | 296 | 192-5 | N | CHOH-BTA | Phenyl |
| 4 | HMBTA | 2 | 149 | 148-52 | N | H | Phenyl |
| 5 | BTA-PCA | 3 | 226 | 110-2 | N | 4-Pyridyl | Phenyl |
| 6 | HMTTA | 2 | 163 | 125-8 | N | H | Tolyl |
| 7 | HMHTTA | 2 | 167 | 48-50 | N | H | Cyclohexyl |
| 8 | BTA-HAA | 1 | 193 | 150-3 | N | COOH | Phenyl |

[a] IA-Inhibitor Activity - 1 = Excellent, 2-Very Good, 3 = Good, 4 = Fair, 5 = Poor and N = None

We claim:

1. A printing ink composition comprising a resin, a solvent and an inhibitor, the inhibitor being a compound having the general formula

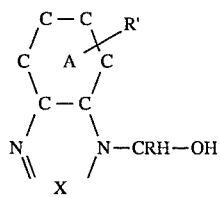

wherein the A ring is benzenoid, napthenoid or saturated cycloaliphatic, the A ring being unsubstituted or substituted with R' which is an alkyl group of 1 to 4 carbon atoms; R is selected from the group consisting of a hydrogen atom, an aryl radical, an alkyl radical, a haloalkyl radical, a haloaryl radical, a 4-pyridyl radical and a carboxy group; and X is a nitrogen atom or the

group, wherein R' is a hydrogen atom or an alkyl group of 1 to 4 carbon atoms, the inhibitor being present in an amount sufficient to inhibit foaming of the ink upon its application as an embossing medium on plastic surfaces.

2. The ink composition of claim 1 wherein the inhibitor is selected from the group consisting of 1-(1-hydroxyethyl) benzotriazole, benzotriazol-1-yl(hydroxy)acetic acid, 1-hydroxymethyl benzotriazole, benzotriazol-1-yl-(4-pyridyl-)methanol, 1-hydroxymethyl tolyl triazole, 1-hydroxymethyl methyl cyclohexyl triazole, and 1-hydroxymethyl benzimidazole.

3. A printing ink composition comprising a resin, a solvent and an inhibitor, the inhibitor being a compound having the formula

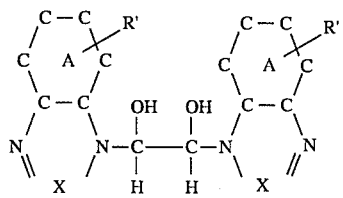

wherein the A ring is benzenoid, napthenoid or saturated cycloaliphatic, the A ring being unsubstituted or substituted with R' which is an alkyl group of 1 to 4 carbon atoms: X is a nitrogen atom or the

group, wherein R' is a hydrogen atom or an alkyl group of 1 to 4 carbon atoms, the inhibitor being present in an amount sufficient to inhibit foaming of the ink upon its application as an embossing medium on plastic surfaces.

4. The ink composition of claim 3, wherein X is a nitrogen atom in each instance.

5. A compound selected from the group consisting of 1-hydroxymethyl tolyl triazole and 1-hydroxymethyl methyl cyclohexyl triazole.

6. The ink composition of claim 3, wherein the inhibitor is 1,2-dibenzotriazol-1-yl ethane-1,2-diol.

* * * * *